(12) United States Patent
Sotzing

(10) Patent No.: US 8,168,671 B2
(45) Date of Patent: May 1, 2012

(54) SYNTHESIS OF THIENO[3,4-B]THIOPHENE, THIENO[3,4-B]FURAN, RELATED COMPOUNDS AND THEIR DERIVATIVES AND USE THEREOF

(75) Inventor: Gregory A. Sotzing, Storrs, CT (US)

(73) Assignee: The University of Connecticut, Farmington, CT (US)

( * ) Notice: Subject to any disclaimer, the term of this patent is extended or adjusted under 35 U.S.C. 154(b) by 150 days.

(21) Appl. No.: 12/480,116

(22) Filed: Jun. 8, 2009

(65) Prior Publication Data

US 2009/0326187 A1    Dec. 31, 2009

Related U.S. Application Data

(60) Provisional application No. 61/075,891, filed on Jun. 26, 2008, provisional application No. 61/096,013, filed on Sep. 11, 2008.

(51) Int. Cl.
| | |
|---|---|
| C07D 209/00 | (2006.01) |
| C07D 495/04 | (2006.01) |
| C07D 493/04 | (2006.01) |
| A61K 31/34 | (2006.01) |
| A61K 31/407 | (2006.01) |
| A61K 31/381 | (2006.01) |

(52) U.S. Cl. ......... 514/412; 548/452; 548/453; 549/32; 549/465; 514/443; 514/469

(58) Field of Classification Search ................... 514/412, 514/443, 469; 548/452, 453; 549/32, 465
See application file for complete search history.

(56) References Cited

U.S. PATENT DOCUMENTS

| | | | |
|---|---|---|---|
| 4,639,328 A | 1/1987 | Krause et al. |
| 4,663,001 A | 5/1987 | Lazzaroni et al. |
| 4,910,645 A | 3/1990 | Jonas et al. |
| 4,959,430 A | 9/1990 | Jonas et al. |
| 4,986,886 A | 1/1991 | Wei et al. |
| 5,109,070 A | 4/1992 | Epstein et al. |
| 5,300,575 A | 4/1994 | Jonas et al. |
| 5,561,030 A | 10/1996 | Holdcroft et al. |
| 5,691,062 A | 11/1997 | Shalaby et al. |
| 6,194,540 B1 | 2/2001 | Ito et al. |
| 6,242,561 B1 | 6/2001 | Mohwald et al. |
| 6,294,245 B1 | 9/2001 | Roitman et al. |
| 6,645,401 B2 | 11/2003 | Giles et al. |
| 7,060,846 B2 | 6/2006 | Zahn et al. |
| 7,071,289 B2 | 7/2006 | Sotzing |
| 7,094,365 B2 | 8/2006 | Zahn et al. |
| 7,118,692 B2 | 10/2006 | Nordquist et al. |
| 7,241,904 B2 | 7/2007 | Zahn et al. |
| 7,270,871 B2 | 9/2007 | Jiang et al. |
| 2002/0011420 A1 | 1/2002 | Roitman et al. |
| 2003/0077515 A1 | 4/2003 | Chen et al. |
| 2004/0074779 A1 | 4/2004 | Sotzing |
| 2005/0124784 A1 | 6/2005 | Sotzing |
| 2005/0209419 A1 | 9/2005 | Zahn et al. |
| 2006/0147616 A1 | 7/2006 | Gaudiana et al. |
| 2006/0223977 A1 | 10/2006 | Zahn et al. |

FOREIGN PATENT DOCUMENTS

| | | |
|---|---|---|
| CA | 2343444 A1 | 3/2000 |
| EP | 0999242 A1 | 5/2000 |
| EP | 1510535 A1 | 3/2005 |
| EP | 1510535 A1 * | 3/2005 |
| WO | 9106887 A1 | 5/1991 |

OTHER PUBLICATIONS

Bongini et al., New n-Dopable Thiophene Based Polymers, Synthetic Metals 101 (1999), pp. 13-14.

Eldo et al., New Low Band Gap Polyers: Control of Optical and Electronic Properties in near Infrared Absorbing . . . Chemistry Materials, 2002, 14, pp. 410-418.

Glenis et al., Polyfuran: A New Synthetic Approach and Electronic Properties, J. Am. Chem. Soc., 115, pp. 12519-12525 (1993).

Gu, Synthesis and Characterization of Poly(2-decylthieno(3,4-b)thiophene), Chem Abstract, 125, 87896 (1996).

Gu, Xiaomin, Part I: Synthesis and Characterization of Poly (2-Decylthieno [3,4-b] Thiopene), A Low BandGap Conducting Polymer Part II: Formation and Trapping of Methoxy (Methoxycarbonyl) Ketene, Dissertation, Dec. 1995, 182 pgs. University of Texas at Arlington.

Kumar et al., Poly(thieno[3,4-b]furan) A New Low Band Gap Conjugated Polymer, Macromolecules, vol. 39, No. 8, pp. 2724-2725, Apr. 18, 2006.

Lee et al., Thienol[3,4-b]thiophene as a new Novel Low Oxidation Crosslinking Agent, Polymeric Materials, Science and Engineering 2002, 86, p. 195.

Lee et al., Synthesis and Characterization of a Soluble and Transparent Conducting Polymer, Poly (3,4-Ethylenedioxythiophene), Mol. Cryst. 1999, vol. 237, pp. 237-240.

Lee et al., Synthesis of Poly(Thieno[3,4-b]thiophene) and its electrochemical characterization, Polymer Preprints 2001, 42(2), pp. 413-414.

Lee et al., Aqueous phase Polymerization of Thieno[3,4-b]Thiophene, Polymer Preprints 2002, 43 (2) pp. 568-569.

Lee et al., Poly(thieno[3,4-b]thiophene), A New Stable Low Band Gap Conducting Polyer, Macromolecules 2001, pp. 5746-5747.

(Continued)

Primary Examiner — Kamal Saeed
Assistant Examiner — Janet L Coppins
(74) Attorney, Agent, or Firm — Cantor Colburn LLP

(57) ABSTRACT

Inexpensive and facile methods of preparing fused heterocycles such as thieno[3,4-b]thiophene, thieno[3,4-b]furan, related compounds, and their derivatives are disclosed. Also disclosed are regioregular polymers prepared from the fused heterocycles.

20 Claims, No Drawings

OTHER PUBLICATIONS

Lee et al., Toward the Use of Poly(Thieno[3,4-b]Thiophene) in Optoelectronic Devices, Polymer Preprints 2002, 43(2), pp. 610-611.

Loveday et al., Synthesis and Characterization of p- and n- Dopable Polymers Electrochromic Properties of Poly3-(p-trimethylammoniumphenyl)bithiophene, Synthetic Metals 84 (1997) pp. 245-246.

Meng et al., A Robust Low Band Gap Processable n-Type Conducting Polymer Based on Poly(isothianaphthene), Macromolecules, 2001, 34, pp. 1810-1816.

Moursounidis et al., The Synthesis of Thieno[3,4-b] Furan Using a Tandem Intramolecular-Reverse Diels-Alder Reaction Approach, Tetrahedron Letters, vol. 27, No. 26, pp. 3045-3048, 1986.

Neef et al., Synthesis and Electronic Properties of Poly(2-phenylthieno[3,4-b]thiophen), American Chemical Society, 128, 230943 (1998).

Neef et al., Synthesis and Electronic Properties of Poly(2-phenylthieno[3,4-b]thiophen), American Chemical Society, 131, 214964 (1999).

Neef et al., Synthesis and Electronic Properties of Poly(2-Phenylthieno[3,4-b]Thiophene) Polymer Preprints 1998, 39 (1) pp. 147-148.

Neef et al., Synthesis and Electronic Properties of Poly(2-Phenylthieno[3,4-b]Thiophene) : A new Low Band Gap Polymer, Chemistry Materials 1999, 11, pp. 1957-1958.

Pomerantz et al., A New Soluble Low-Bandgap Conducting Polymer, Elservier, 126, 293709 (1997).

Pomerantz et al., Poly(2-decylthieno[3,4-b]thiophene-4,6-diyl) A New Low Band Gap Conducting Polymer, Macromolecules 2001, 34, pp. 1817-1822.

Pomerantz et al., Poly(2-decylthieno[3,4-b]thiophene), A New Soluble Low-Bandgap Conducting Polymer, Synthetic Metals 84 (1997) pp. 243-244.

Reeves et al., Dual Cathodically and Anodically Coloring Electrochromic Polymer Based on a Spiro Bipropylenedioxythiophene [(Poly(spiroBiProDOT)], Advanced Materials, May 17, 2002, vol. 14, No. 10, 717-719.

Roncali et al., Enhancement of the Mean Conjugation Length in Conducting Polythiophenes, Synthetic Metals, 1987, vol. 18, 139-144.

Seshadri et al., Ion Transport Behavior of Polymers and Copolymers Containing Thieno [3,4-b]Thiophene Polymer Preprints 2002, 43 (2) pp. 584-585.

Song Y. Hong et al., Understanding the Conformational Stability and Electronic Structures of Modified Polymers Based on Polythiopene, Macromolecules 1992, pp. 4652-4657.

Sotzing et al., Preparation and Characterization of Fully conjugated Intrinsically conducting Polymer Networks, Polymeric Materials: Science and Engineering, 2002, 86, pp. 40-41.

Sotzing et al., Poly(thieno[3,4-b]thiophene) as a Low Band Gap Conducting Polymer and Electrochromic Material, Polymeric Materials: Science and Engineering 2001, 85, pp. 604-605.

Sotzing et al., Intrinsically Conducting Polymers and Green Chemistry, Polymer Preprints, 2002, 43(2), 904-905.

Wynberg et al., Thieno[3,4-b]Thiophene. The Third Thiophthene Tetrahedron Letters, No. 9, 1967, pp. 761-764.

* cited by examiner

SYNTHESIS OF THIENO[3,4-B]THIOPHENE, THIENO[3,4-B]FURAN, RELATED COMPOUNDS AND THEIR DERIVATIVES AND USE THEREOF

CROSS REFERENCE TO RELATED APPLICATION

This application claims the benefit of U.S. Provisional Application Ser. Nos. 61/075,891 filed Jun. 26, 2008 and 61/096,013 filed Sep. 11, 2008, each of which is hereby incorporated by reference in its entirety.

TECHNICAL FIELD

This invention relates to methods of making fused heterocycles such as thieno[3,4-b]thiophene, thieno[3,4-b]furan, related compounds, and their derivatives. Also disclosed are polymers prepared from the fused heterocycles and uses thereof.

BACKGROUND

Thieno[3,4-b]thiophene and thieno[3,4-b]furan are known compounds that are useful as monomers in the preparation of intrinsically conducting polymers. A known method of preparing thieno[3,4-b]thiophene requires an expensive starting material 3,4-dibromothiophene. Furthermore, this process does not allow for the easy derivatization of the 2 position of the thieno[3,4-b]thiophene, thereby limiting the flexibility of the process.

There remains a continuing need in the art for new, inexpensive, and facile processes to prepare thieno[3,4-b]thiophene, thieno[3,4-b]furan, and related compounds. Furthermore, there is a continuing need for a facile process to prepare derivatives of these fused heterocycles.

BRIEF SUMMARY OF THE INVENTION

In one embodiment, a method of making a method of making a fused heterocycle comprises using a compound according to formula (I) or a suitably protected derivative thereof as a starting material:

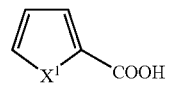

(I)

to form a fused heterocycle of formula (II)

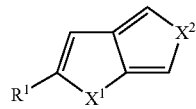

(II)

wherein $X^1$ is S, O, N—$R^1$ or P—$R^2$, wherein $R^1$ is hydrogen or a nitrogen protecting group, and $R^2$ is hydrogen or a phosphorus protecting group; $X^2$ is S, O, N—$R^1$, or P—$R^2$, where $R^1$ and $R^2$ are as previously defined; and R is hydrogen, $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, halo, amino, or mono- or dialkyl amino.

In another embodiment, a regioregular polymer comprises a regioregular fused heterocycle polymer of formula (III)

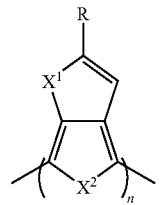

(III)

wherein $X^1$ is S, O, N—$R^1$ or P—$R^2$, wherein $R^1$ is hydrogen or a nitrogen protecting group, and $R^2$ is hydrogen or a phosphorus protecting group; $X^2$ is S, O, N—$R^1$, or P—$R^2$, where $R^1$ and $R^2$ are as previously defined; and R is $C_1$-$C_{20}$ alkyl, heteroalkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, halo, amino, or mono- or dialkyl amino.

In yet another embodiment, a process of preparing a regioregular polymer comprises reacting a monomeric composition comprising a fused heterocycle of formula (V)

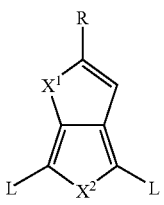

(IV)

with a haloorganomagnesium reagent to form an organometallic intermediate; and polymerizing the organometallic intermediate in the presence of a Ni(II) catalyst to form a regioregular fused heterocycle polymer of formula (III)

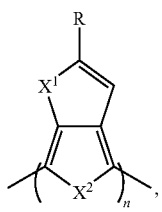

(III)

wherein $X^1$ is S, O, N—$R^1$, or P—$R^2$, wherein $R^1$ is hydrogen or a nitrogen protecting group, and $R^2$ is hydrogen or a phosphorus protecting group; $X^2$ is S, O, N—$R^1$, or P—$R^2$ where $R^1$ and $R^2$ are as previously defined; R is $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, amino, or mono- or dialkyl amino; and L is a leaving group.

DETAILED DESCRIPTION OF THE INVENTION

Disclosed herein are facile methods of preparing fused heterocycles thieno[3,4-b]thiophene, thieno[3,4-b]furan, and related compounds starting with an inexpensive starting material (e.g., thiophene-2-carboxylic acid, furan-2-carboxylic acid, pyrrole-2-carboxylic acid, 2-substituted phospholes prepared using the method disclosed in E. Deschamps and F. Mathey, Bull. Soc. Chim. Fr. (1992), Vol. 129, p. 486-489), etc. A further advantage of the methods is that intermediate compounds can be isolated in sufficient purity without a purification step, such that a purification of the final compound provides a pure product. Thus, the process itself is inexpensive.

Also disclosed are facile methods of preparing 2-substituted thieno[3,4-b]thiophene, thieno[3,4-b]furan, and related compounds. Such derivitization allows for the synthesis of intrinsically conductive polymers having varied electronic and optoelectronic properties as the substitution can affect the band gap (Eg) of the polymer. Furthermore, derivitization can also be used to tailor the solubility in a given solvent system of a polymer formed from the monomers.

Also disclosed are regioregular polymers prepared from the fused heterocycles and methods of preparing the regioregular polymers.

The methods to prepare thieno[3,4-b]thiophene, thieno[3,4-b]furan, related compounds, and derivatives thereof can generally be described according to the following reaction scheme wherein a compound of Formula I is used to prepare a fused heterocycle compound of Formula II. According to Formulas I and II, $X^1$ is S,

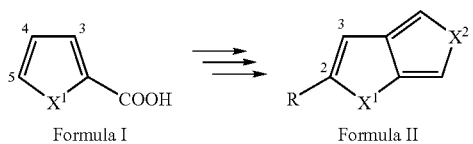

Formula I                Formula II

O, N—$R^1$ or P—$R^2$, wherein $R^1$ is hydrogen or a nitrogen protecting group and $R^2$ is hydrogen or a phosphorus protecting group; $X^2$ is S, O, N—$R^1$ or P—$R^2$, where $R^1$ and $R^2$ are as previously defined; and R is hydrogen, $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, halo, amino, or mono- or di alkyl amino. Exemplary nitrogen or phosphorous protecting groups include linear or branched alkyl, trialkylsilyl, or phenylsulfonyl groups.

In one embodiment, the compound of Formula I is protected at the 5 position with a suitable protecting group to allow for further synthetic manipulations to the remaining free position(s) on the ring structure. Exemplary protecting groups include alkylsilanes and the like. A specific example of a protecting group is trimethylsilyl. Choice of a protecting group can be made by one having ordinary skill in the art without using undue experimentation. Guidance for choosing such groups can be found in, for example, Greene et al. "Protecting Groups in Organic Synthesis" ($2^{nd}$ ed.) J. Wiley & Sons, 1991. Processes for deprotecting can also be found in the same reference.

A compound of Formula I, or its corresponding derivative having a protecting group at the 5 position, is carboxylated at the 3 position to form a dicarboxylic acid intermediate. Known processes to carry out the carboxylation step include metallation followed by reaction with carbon dioxide or formic acid; or a two-step procedure via a reaction with a chloroesterformate followed by hydrolysis.

In another embodiment, the dicarboxylic acid intermediate is derivitized at the 5 position using electrophilic or nucleophilic chemistries known in the art. In one embodiment, the derivatization is performed using aromatic electrophilic substitution including, for example, nitration, sulfonation, alkylation, formylation, etc. In another embodiment, the derivitization is performed using nucleophilic chemistries, for example first a deprotonation using a suitable base such as an alkyllithium (e.g., lithium diisopropylamide) followed by an electrophile such as an alkyl halide (alkylation), acyl halide (to produce a ketone or aldehyde functionality; or a carboxylic acid functionality if a chloroesterformate is used followed by hydrolysis).

In one embodiment, the derivitization involves metallation of the dicarboxylic acid intermediate at the 5 position followed by alkylation using a haloalkyl reagent. Exemplary reagents for metallation include alkyllithium compounds such as n-butyllithium, tert-butyllithium, etc. Exemplary haloalkyl reagents include chloro, bromo, or iodo alkanes having 1-20 carbon atoms. Exemplary alkyl groups of the haloalkyl include methyl, ethyl, n-propyl, isopropyl, n-butyl, tert-butyl, iso-butyl, n-pentyl, iso-pentyl, neo-pentyl, n-hexyl, 2-methylpentyl, 3-methylpentyl, 2,3-dimethylbutyl, 2,2-dimethylbutyl, n-heptyl, n-octyl, n-nonyl, n-decyl, n-undecyl, n-dodecyl, and isomers thereof.

A nitration reaction on the dicarboxylic acid intermediate can be carried out using nitronium tetrafluoroborate, or the processes and reagents as described in March "Advanced Organic Chemistry" ($4^{th}$ ed.) J. Wiley & Sons, 1992 pp. 522-525 and references cited therein.

The dicarboxylic acid or its derivitized derivative is then subjected to a reduction to convert the carboxylic acids at the 2 and 3 positions to hydroxyl groups. The reduction can be carried out by know processes as described in March "Advanced Organic Chemistry" ($4^{th}$ ed.) J. Wiley & Sons, 1992 p. 1212 and references cited therein. Suitable reducing agents include lithium aluminum hydride (LiAlH$_4$), borane, aluminum hydride, or samarium (II) iodide (SmI$_2$) in basic media.

In one embodiment, the dicarboxylic acids can be converted to carboxylic esters and subsequently reduced to hydroxyl groups. Exemplary processes to reduce carboxylic esters can be found in March "Advanced Organic Chemistry" ($4^{th}$ ed.) J. Wiley & Sons, 1992 p. 1214 and references cited therein. Exemplary reducing agents include lithium aluminum hydride, diisobutylaluminium hydride (DIBALH), lithium triethyl borohydride, BH$_3$—SMe$_2$. Formation of carboxylic esters from carboxylic acid groups are well known. Exemplary processes can be found in March "Advanced Organic Chemistry" ($4^{th}$ ed.) J. Wiley & Sons, 1992 p. 1281-1282 and references cited therein.

In another embodiment, the carboxylic acid groups can be converted to an acyl halide using thionyl chloride, oxalyl chloride, phosphorus trichloride (PCl$_3$), phosphorus tribromide (PBr$_3$), or phosphorus pentachloride (PCl$_5$).

The resulting hydroxyl groups are converted to leaving groups such as halogens, alkyl sulfonates or aryl sulfonates. Specific leaving groups include chloride, bromide, or iodide. Formation of a halogen leaving group can be achieved by converting the hydroxyl groups using thionyl chloride, PCl$_3$, PCl$_5$, POCl$_3$, PBr$_3$, PBr$_5$, the combination of PPh$_3$ and CCl$_4$ or CBr$_4$; and by the processes described in March "Advanced Organic Chemistry" ($4^{th}$ ed.) J. Wiley & Sons, 1992 pp. 431-433 and references cited therein. Suitable reactions for preparing alkyl sulfonates from alcohols and sulfonic acid halides can be found in March "Advanced Organic Chemistry" ($4^{th}$ ed.) J. Wiley & Sons, 1992 pp. 498-499 and references cited therein.

The intermediate compound with the leaving groups is cyclized to form a compound comprising a dihydrothienyl, dihydrofuranyl, dihydropyrrolyl moiety, or dihydrophospholyl moiety which is then aromatized to form a compound according to Formula II. The cyclization to form a dihydrothienyl moiety can be carried out by an aliphatic nucleophilic substitution reaction with an appropriate sulfur source such as sodium sulfide or a hydrate thereof, or hydrogen sulfide. Examples of alkyl-thiodehalogenation reactions are described in March "Advanced Organic Chemistry" (4$^{th}$ ed.) J. Wiley & Sons, 1992 pp. 407-408 and references cited therein.

To form the dihydrofuranyl moiety, the compound with the leaving groups, specifically halogen groups, can be converted to an ether by treatment with hydroxide, or an oxide ion which can be generated in situ by reacting an organotin oxide and fluoride ion in the presence of a quaternary ammonium iodide or crown ether. Exemplary processes are described in March "Advanced Organic Chemistry" (4$^{th}$ ed.) J. Wiley & Sons, 1992 pp. 402-403 and references cited therein.

To form the dihydropyrrolyl moiety, the compound with the leaving groups, specifically halogen groups, can be converted to a dihydropyrrolyl moiety by reaction with a sodium or calcium salt of cyanamide $NH_2$—CN, optionally under phase transfer conditions, and other reagents typically used for Knorr and Paal-Knorr pyrrole ring closure processes. Exemplary processes are described in March "Advanced Organic Chemistry" (4$^{th}$ ed.) J. Wiley & Sons, 1992 p. 413 and references cited therein.

To form the dihydrophospholyl moiety, the compound with the leaving groups, specifically halogen groups, can be converted to a dihydrophospholyl moiety by reaction with a phosphine or a monoalkylsubstituted phosphine to produce the P-protected analog using similar procedures as used to prepare the dihydropyrrolyl moiety.

The dihydro analogs of Formula II can be aromatized to the compounds of Formula II using well-known methods and reagents in the art. Exemplary oxidizing agents include 2,3-dichloro-5,6-dicyano-1,4-benzoquinone (DDQ), 2,3,5,6-tetrachloro-1,4-benzoquinone (chloranil), oxygen, $MnO_2$, $SeO_2$, chromic acid, etc. Exemplary reagents and processes to aromatize can be found in March "Advanced Organic Chemistry" (4$^{th}$ ed.) J. Wiley & Sons, 1992 pp. 1163-1164 and references cited therein.

If the compound of Formula I was protected at the 5 position, the protecting group can be removed prior to or after the aromatization step to form the compound of Formula II. Suitable deprotecting processes include using a fluoride source (e.g., tetra-n-butylammonium fluoride, "TBAF") if the protecting group was an alkyl or arylsilane group.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, "—CHO" is attached through carbon of the carbonyl group.

Unless otherwise indicated, the term "substituted" as used herein means replacement of one or more hydrogens with one or more substituents. Suitable substituents include, for example, hydroxyl, $C_6$-$C_{12}$ aryl, $C_3$-$C_{20}$ cycloalkyl, $C_1$-$C_{20}$ alkyl, halogen, $C_1$-$C_{20}$ alkoxy, $C_1$-$C_{20}$ alkylthio, $C_1$-$C_{20}$ haloalkyl, $C_6$-$C_{12}$ haloaryl, pyridyl, cyano, thiocyanato, nitro, amino, $C_1$-$C_{12}$ alkylamino, $C_1$-$C_{12}$ aminoalkyl, acyl, sulfoxyl, sulfonyl, amido, or carbamoyl.

As used herein, "alkyl" includes straight chain, branched, and cyclic saturated aliphatic hydrocarbon groups, having the specified number of carbon atoms, generally from 1 to about 20 carbon atoms, greater than 3 for the cyclic. Alkyl groups described herein typically have from 1 to about 20, specifically 3 to about 18, and more specifically about 6 to about 12 carbons atoms. Examples of alkyl include, but are not limited to, methyl, ethyl, n-propyl, isopropyl, n-butyl, 3-methylbutyl, t-butyl, n-pentyl, and sec-pentyl. As used herein, "cycloalkyl" indicates a monocyclic or multicyclic saturated or unsaturated hydrocarbon ring group, having the specified number of carbon atoms, usually from 3 to about 10 ring carbon atoms. Monocyclic cycloalkyl groups typically have from 3 to about 8 carbon ring atoms or from 3 to about 7 carbon ring atoms. Multicyclic cycloalkyl groups may have 2 or 3 fused cycloalkyl rings or contain bridged or caged cycloalkyl groups. Examples of cycloalkyl groups include cyclopropyl, cyclobutyl, cyclopentyl, or cyclohexyl as well as bridged or caged saturated ring groups such as norbornane or adamantane.

As used herein "haloalkyl" indicates both branched and straight-chain alkyl groups having the specified number of carbon atoms, substituted with 1 or more halogen atoms, generally up to the maximum allowable number of halogen atoms ("perhalogenated"). Examples of haloalkyl include, but are not limited to, trifluoromethyl, difluoromethyl, 2-fluoroethyl, and penta-fluoroethyl.

As used herein, "alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

As used herein "heteroaryl" indicates aromatic groups containing carbon and one or more heteroatoms chosen from N, O, and S. Exemplary heteroaryls include oxazole, pyridine, pyrazole, thiophene, furan, isoquinoline, and the like. The heteroaryl groups may be substituted with one or more substituents.

As used herein, "halo" or "halogen" refers to fluoro, chloro, bromo, or iodo.

The fused heterocycles can be used as monomers for the preparation of intrinsically conductive polymers such as those described in U.S. Pat. No. 7,332,223 to Sotzing et al., U.S. Pat. No. 7,321,012 to Sotzing, U.S. Pat. No. 7,125,479 to Sotzing, U.S. Pat. No. 7,071,289 to Sotzing et al.; and PCT International Publication No. WO2007/008977 A1 to Sotzing as well as the uses and devices described therein.

The fused heterocycle monomers can be prepared into polymers and copolymers using a variety of processes. In one embodiment, a polymer is prepared via an electrochemical process wherein one or more types of heterocycle monomers are polymerized in an electrochemical cell using a three electrode configuration. An exemplary three electrode configuration comprises a button working electrode such as platinum, gold or vitreous carbon button working electrodes, a platinum flag counter electrode, and an AgAg+ non-aqueous reference electrode. Exemplary suitable electrolytes include tetrabutylammonium perchlorate/acetonitrile, lithium triflate/acetonitrile and tetrabutylammonium hexafluorophosphate/acetonitrile, and the like.

The polymer can be prepared onto the surface of a working electrode and then removed by washing with a solvent such as acetonitrile.

Conventional electrolytic cells can be utilized to practice the electrochemical process for making the polymers. In one embodiment, the working electrode is a vitreous carbon electrode and the electrolyte is tetrabutylammonium perchlorate/acetonitrile.

Alternatively, the polymers can be prepared via a chemical process, specifically an aqueous phase polymerization method wherein the fused heterocycle monomer, a polyanion and an oxidant are reacted in the presence of water under reaction conditions sufficient to form a polymer. Alternatively, the polymers can be prepared via a chemical process in the presence of organic solvents, including halogenated solvents such as methylene chloride and chloroform, and non-halogenated solvents such as toluene, dimethylformamide, dimethylacetamide, dimethylsulfoxide, acetonitrile, nitromethane, nitrobenzene, and the like.

Typical reaction conditions include temperatures ranging from 0° C. to about 50° C. The polymerization is continued for a period of time until the reaction in completed to effect the desired degree of polymerization. The degree of polymerization can vary depending upon the end use application as is readily determined by one of ordinary skill in the art without undue experimentation. The polymerization time may range from a few minutes up to about 48 hours and depends on a number of factors including the size of the reactor utilized in the polymerization, the polymerization temperature, and the oxidant utilized in the polymerization process.

The amount of polyanion and oxidant to be employed in the aqueous polymerization method may broadly vary and can be determined for any given polymerization without undue experimentation. For example the weight ratio of fused heterocycle monomer to a desired polyanion typically ranges from about 0.001 to about 10, specifically about 0.05 to about 1.0. The weight ratio of fused heterocycle monomer to a desired oxidant typically ranges from about 0.01 to about 10, specifically about 0.1 to about 2.0.

Exemplary suitable polyanions include an anion of a polycarboxylic acid, such as polyacrylic acid, polymethacrylic acid, perfluorosulfonic acid polymers commercially available from, for example, E.I. DuPont de Nemours & Co. under the trade name NAFION, polymaleic acid, and polymeric sulfonic acids, such as polystyrene sulfonic acid and polyvinyl sulfonic acid. The polycarboxylic and polysulfonic acids may also be copolymers of vinyl carboxylic and vinyl sulfonic acids with other monomers, such as acrylates and styrene. The molecular weight of the acids supplying the polyanions can be in the range from about 1,000 to about 500,000, specifically from about 2000 to about 500,000, and more specifically about 70,000. The acids from which the polyanions are derived are commercially available or may be produced by known methods.

Suitable chemical oxidants include iron (III) salts, such as $FeCl_3$, $Fe(ClO_4)_3$ and the iron (III) salts of organic acids and inorganic acids containing organic residues, $H_2O_2$, $K_2Cr_2O_7$, alkali or ammonium persulfates, alkali perborates, potassium permanganate and copper salts such as copper tetrafluoroborate. In addition, iodine, air, and oxygen may advantageously be used as oxidants.

Examples of iron (III) salts of organic acids are the Fe(III) salts of $C_1$-$C_{30}$ alkyl sulfonic acids, such as methane or dodecane sulfonic acid; aliphatic $C_1$-$C_{20}$ carboxylic acids, such as 2-ethylhexylcarboxylic acid, aliphatic perfluorocarboxylic acids, such as trifluoroacetic acid and perfluorooctanoic acid; aliphatic dicarboxylic acids, such as oxalic acid, and, aromatic, optionally $C_1$-$C_{20}$-alkyl-substituted sulfonic acids, such as benzenesulfonic acid, p-toluene-sulfonic acid, and dodecyl benzenesulfonic acid and mixtures of the aforementioned Fe(III) salts of organic acids. Examples of iron (III) salts of inorganic acids containing organic residues are the iron (III) salts of sulfuric acid semiesters of $C_1$-$C_{20}$ alkanols, for example the Fe(III) salt of lauryl sulfate. The ratio of chemical oxidant to fused heterocycle monomer can be about 1:1 to about 4:1.

The electrochemical method and chemical polymerization method may be used to conduct a homopolymerization or a copolymerization of the fused heterocycle monomer, and optionally with one or more co-monomers.

In a specific embodiment, the fused heterocycle monomers are polymerized into regioregular polymers. One method of preparing the regioregular polymer is to convert the fused heterocycle monomer into a monomer having leaving groups, such as a halogen, positioned at the 4 and 6 positions of the heterocycle ring. Exemplary monomers are 4,6-dibromo and 4,6-diiodo fused heterocycle monomers. The 4,6-leaving group substituted fused heterocycle monomer can be treated with a haloorganomagnesium reagent to form an organometallic monomer intermediate which is subsequently polymerized in the presence of a catalyst known to provide regioregular polymerization (head-to-tail).

In an exemplary preparation of the 4,6-leaving group substituted fused heterocycle monomer, the fused heterocycle monomer is halogenated, for example using N-bromosuccinimide (NBS).

The haloorganomagnesium reagent can include alkyl, vinyl, or phenyl halomagnesium reagents. Exemplary haloorganomagnesium reagents include hexylmagnesium bromide and other well-known Grignard reagents.

The catalyst for the regioregular polymerization can be a Ni(II) catalyst such as 1,3-diphenylphosphinopropane nickel (II) chloride and 1,2-bis(diphenylphosphino)ethane nickel (II) chloride.

In another embodiment, Rieke zinc can be used in place of the haloorganomagnesium reagent to form the organometallic monomer intermediate that is polymerized in the presence of the nickel catalyst.

In one embodiment, a method of preparing a regioregular polymer comprises reacting a monomeric composition comprising a fused heterocycle of formula (IV)

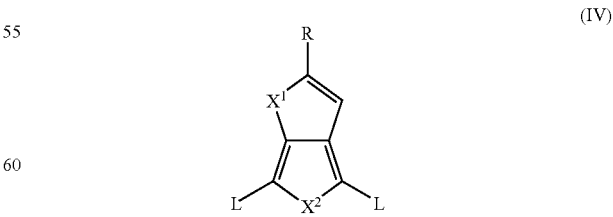

(IV)

with a haloorganomagnesium reagent to form an organometallic intermediate; and polymerizing the organometallic intermediate in the presence of a Ni(II) catalyst to form a regioregular fused heterocycle polymer of formula (III)

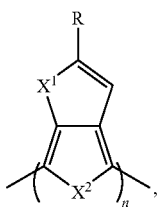

(III)

wherein $X^1$ is S, O, N—$R^1$, or P—$R^2$ wherein $R^1$ is hydrogen or a nitrogen protecting group, and $R^2$ is hydrogen or a phosphorus protecting group; $X^2$ is S, O, N—$R^1$, or P—$R^2$ where $R^1$ and $R^2$ are as previously defined; R is $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, amino, or mono- or di alkyl amino; and L is a leaving group. In another embodiment, the leaving group is a bromo or iodo group. In yet another embodiment, the haloorganomagnesium reagent is a bromoalkylmagnesium reagent. In still yet another embodiment, the Ni(II) catalyst is 1,3-diphenylphosphinopropane nickel(II) chloride or 1,2-bis(diphenylphosphino)ethane nickel(II) chloride. In one embodiment, the fused heterocycle of formula (IV)

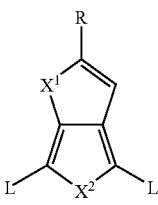

(IV)

is prepared from a fused heterocycle of formula (II)

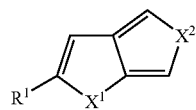

(II)

wherein L, R, $X^1$, and $X^2$ have been previously defined.

Other methods of preparing regioregular polymers include Stille and Suzuki coupling by preparing the fused heterocycle monomers into the appropriate tin and boron intermediates followed by polymerization with a palladium catalyst.

In one embodiment, a regioregular polymer comprises a regioregular fused heterocycle polymer of formula (III)

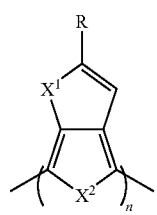

(III)

wherein $X^1$ is S, O, N—$R^1$ or P—$R^2$, wherein $R^1$ is hydrogen or a nitrogen protecting group, and $R^2$ is hydrogen or a phosphorus protecting group; $X^2$ is S, O, N—$R^1$, or P—$R^2$, where $R^1$ and $R^2$ are as previously defined; and R is $C_1$-$C_{20}$ alkyl, heteroalkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, halo, amino, or mono- or dialkyl amino. In a specific embodiment, $X^1$ is S, O or N—$R^1$ and $X^2$ is S, O, or N—$R^1$. In yet another embodiment, $X^1$ is S or O and $X^2$ is S or O. In still another embodiment, $X^1$ is S and $X^2$ is S. In yet another embodiment, R is $C_{10}$-$C_{20}$ alkyl. In a further embodiment, R is $C_5$-$C_{15}$ alkyl, specifically $C_6$-$C_{12}$ alkyl. In another embodiment, R is methyl, ethyl, n-propyl, isopropyl, n-butyl, tert-butyl, iso-butyl, n-pentyl, iso-pentyl, neo-pentyl, n-hexyl, 2-methylpentyl, 3-methylpentyl, 2,3-dim ethylbutyl, 2,2-dimethylbutyl, n-heptyl, n-octyl, n-nonyl, n-decyl, n-undecyl, or n-dodecyl.

The homopolymers and copolymers described herein may be used in the form of dispersions comprising the polymer and an organic or aqueous liquid carrier. It is to be understood that the term "dispersion" as used herein is inclusive of compositions wherein none or a portion of the polymer is fully dissolved in the liquid. Specifically, the polymers of the dispersion are in the form of small particles that are storage stable, i.e., remain in substantially the same particulate form for at least about 24 hours, more specifically at least about 48 hours, even more specifically at least about one week, and yet more specifically at least about one month. In one embodiment, the liquid carrier is the same as the solvent in which the polymers are manufactured, preferably water or one or more water-miscible organic solvents. Of course, additional solvent may be used to dilute the dispersion if desired. The amount of the polymer in the dispersion may vary from about 1 to about 99 percent by weight depending upon a variety of factors, for example, the nature of the solvent, the nature of the polymer, the molecular weight of the polymer, and the end-use application, and is readily determined by one of ordinary skill in the art without undue experimentation.

Dispersions or solutions containing the fused heterocycle polymers can be formed into films by applying the dispersions or solutions to a substrate via conventional processes including ink jet printing, screen printing, roll to roll printing processes, reel to reel processing, spin coating, meniscus and dip coating, spray coating, brush coating, doctor blade application, curtain casting, drop casting, and the like, to form a layer. Suitable substrates are solid materials (flexible or rigid) suitable for deposition of the polymeric compositions, and may be, for example, glass, an organic polymer such as a plastic, silicon, a mineral, a semiconducting material, a ceramic, a metal, and the like, as well as a combination comprising at least one of the foregoing materials. The substrate may be inherently conductive.

The liquid may be removed from the layer of the dispersion or solution by conventional techniques to form a film. Removal of the liquid may be effected at room temperature or other temperature that does not adversely affect the properties of the resulting film. However, to obtain higher processing speeds, the film can be dried at elevated temperatures.

The electrical conductivity of the films can be readily modified, if necessary, to meet the requirements of a desired application by doping with conventional acidic dopants (p-dopants) or basic dopants (n-dopants) known in the art. Suitable p-dopants include mineral acids such as HCl, $HNO_3$, $H_2SO_4$, $H_3PO_4$, HBr, and HI; organic sulfonic acids such as dodecyl benzene sulfonic acid, lauryl sulfonic acid, camphor sulfonic acid, organic acid dyes, methane sulfonic acid, and toluene sulfonic acid; polymeric sulfonic acids such as poly (styrene sulfonic acid) and copolymers of styrene sulfonic acids; carboxylic acids such as adipic acid, azelaic acid, and oxalic acid; and polycarboxylic acids such as poly(acrylic acid), poly(maleic acid), poly(methacrylic acid), and copolymers formed from acrylic acid, maleic acid, or methacrylic acid. Conventional mixed dopants comprising one or more of the foregoing, such as a mixture of a mineral acid and an organic acid, can also be used to impart the desired electroactive character to the films. Suitable basic dopants include, but are not limited to Na, K, Li, and Ca. Other suitable dopants include $I_2$, $PF_6$, $SbF_6$, and $FeCl_3$. In some instances the oxidant and the dopant may be the same.

Admixtures of the polymer with other electroactive materials such as laser dyes, other electroactive polymers, hole transport or electron transport materials, including electroactive organometallic compounds, are also contemplated herein. Such materials can be added to the polymer before or after formation of the solution or dispersion. Additives such as ethylene glycol, diethylene glycol, mannitol, propylene 1,3-glycol, butane 1,4-glycol, N-methylpyrrolidone, sorbitol, glycerol, propylene carbonate, and other appropriate high boiling organics may be added to dispersions of the polymeric compositions to improve conductivity.

Additional additives may also be used, and include conductive fillers such as particulate copper, silver, nickel, aluminum, carbon black (carbon nanotubes, buckminister fullerene), and the like; non-conductive fillers such as talc, mica, wollastonite, silica, clay, dyes, pigments (zeolites), and the like, to promote specific properties such as increased modulus, surface hardness, surface color and the like; antioxidants; UV stabilizers; viscosity modifiers; and surfactants such as acetylenic diols, surfactants typically being added to control stability, surface tension, and surface wettability.

The fused heterocycle polymers disclosed herein can be processed by conventional methods to provide uniform, thin films that possess utility in numerous applications. Films and materials comprising the above-described polymers can be utilized in a variety of applications, including antistatic coatings, electrically conductive coatings, electrochromic devices, photovoltaic devices, light emitting diodes for display applications, near infrared light emitting diodes, flat panel displays, flexible displays, photoimageable circuits, printable circuits, thin film transistor devices, batteries, electrical switches, capacitor coatings, corrosion resistant coatings, electromagnetic shielding, sensors, biosensors, dimmable mirrors, type III supercapacitors, LED lighting, and the like. The electrical conductivity of the polymers can be readily modified, if necessary, to meet the requirements of any of the previously mentioned applications by doping the polymers with conventional acidic dopants (p-dopants) and basic dopants (n-dopants) known in the art.

The above-described polymers are particularly well suited for use in fabricating certain components of light emitting diodes (LEDs). LEDs typically comprise a substrate, and indium tin oxide (ITO) anode, a hole injection layer, a hole transport layer, a light emitting layer, an electron transport layer, an electron injection layer, and a cathode. The p-doped polymers are particularly suited for replacing the indium tin oxide anode of the LED, or as the hole injection layer of the LED. Undoped polymers described herein can be utilized in the hole transport layer, the light emitting layer or the electron transport layer of the LED.

The above-described polymers are also particularly well suited for use in fabricating certain components of photovoltaic devices, which are constructed similarly to LEDs. Instead of electrical voltage placed across the device to produce light for the LED device, the input of light (e.g. sunlight) produces a voltage difference across the device to produce an electric current. The devices comprise a light harvesting organic or polymer intermediate layer, with hole transport/electron transport layers optionally placed between the anode and cathode. The polymers can be utilized as the anode and hole injection layers (doped) or in the light harvesting layers (undoped).

The following illustrative examples are provided to further describe how to make and use the polymers and are not intended to limit the scope of the claimed invention.

EXAMPLES

Example 1

Preparation of thieno[3,4-b]thiophene

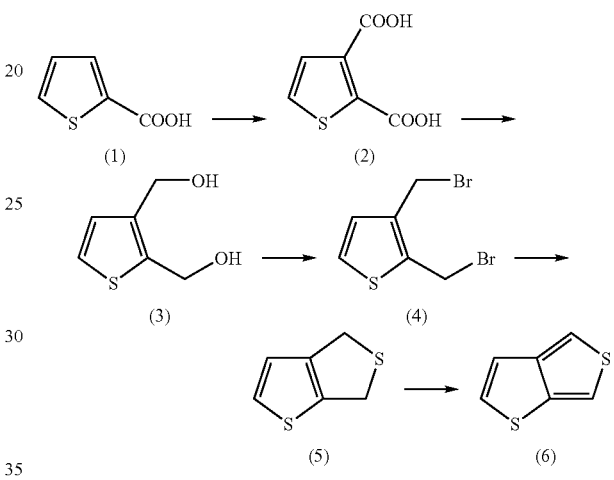

Thiophene-2,3-dicarboxylic acid (2). To a solution of thiophene-2-carboxylic acid (1, 20 g, 156 mmol), in anhydrous THF (500 mL), at −78° C. was added a 2.5 M solution of n-BuLi in hexane (137.2 mL, 342 mmol) over a period of 90 mins. The reaction was allowed to stir at −78° C. for another 30 mins at which time it was quenched with $CO_2$. Upon addition of $CO_2$, the reaction became very thick and required some shaking for efficient mixing. The reaction was allowed to warm at room temperature and stirring continued for another 8 hrs. The reaction was quenched by 200 mL of water and 80% THF was removed by using a rotovap. The aqueous layer was acidified with dilute HCl (until cloudy) and kept for 4 hrs. The crude acid was precipitated out from the aqueous layer, filtered and dried. The crude acid solid was recrystallized from isopropanol to provide pure 2 (13 g, 51% yield), which was confirmed by $^1$H-NMR.

2,3Bis(hydroxymethyl)thiophene (3). To a slurry of $LiAlH_4$ (16.5 g, 434 mmol), in THF (500 mL) at 0° C., under an atmosphere of nitrogen, was added thiophene-2,3-dicarboxylic acid (2, 15 g, 87.2 mmol). The reaction was allowed to warm to 70° C. and was stirred for another 24 hrs. After 24 hrs the reaction flask was kept in an ice bath and then 50 mL of diethyl ether was added followed by the addition of 15 mL of water and 15 mL of 10% NaOH solution. Addition of water was drop-wise. The organic layer was dried over $MgSO_4$, filtered and the filtrate concentrated to a crude solid 3 (9.4 g, 75% yield) confirmed by $^1$H-NMR.

2,3Bis(bromomethyl)thiophene (4). To a solution of 2,3bis (hydroxymethyl)thiophene (3, 10 g, 69.4 mmol) in anhydrous ether (400 mL) at 0° C., under a nitrogen atmosphere, was added $PBr_3$ (9.8 mL, 104 mmol) drop-wise over a period of 15 mins. The reaction was continued for another 6 hrs at room temperature and quenched by adding 50 mL of water. The organic layer was extracted 4-5 times with water until the pH became neutral. The organic layer was dried over MgSO$_4$, filtered and the filtrate concentrated to a white solid 4 (15 g, 80% yield) confirmed by $^1$H-NMR and GC-MS.

Dihydrothieno[3,4-b]thiophene (5). To a solution of sodium sulfide nonahydrate (8.9 g, 37 mmol) in DMF (100 mL) at 30° C. under a nitrogen atmosphere, was added 2,3 bis(bromomethyl)thiophene (4, 10 g, 37 mmol) solution in DMF (300 mL). 2,3Bis(bromomethyl)thiophene addition was very slow and the temperature monitored to gradually increase from 30° C. to 70° C. The reaction was continued for another 12 hrs at 70° C. during which time the contents became dark in color. The product was extracted in diethyl ether (200 mL) and washed with sufficient water to remove DMF. The organic layer was dried over MgSO$_4$, filtered and the filtrate concentrated to a crude dark brown liquid 5 (2.1 g, 40% yield). The product was confirmed by $^1$H-NMR and GC-MS.

Thieno[3,4-b]thiophene (6). Dihydrothieno[3,4-b]thiophene (2 g, 14 mmol) and anhydrous methylene chloride (100 mL) were taken in a dry 3-neck flask, and cooled the solution to 0° C. before adding 2,3-dichloro5,6-dicyano-1,4-benzoquinone (DDQ, 3.17 g, 14 mmol). The reaction mixture was stirred at 0° C. for 30 minutes, and then passed through the silica. After evaporating the solvent, the product was purified by liquid chromatography using petroleum ether as an eluent. The purified thieno[3,4-b]thiophene 6 was obtained (1 g, 50% yield). The final product was confirmed by $^1$H-NMR and GC-MS.

Example 2

Preparation of 2-hexylthieno[3,4-b]thiophene

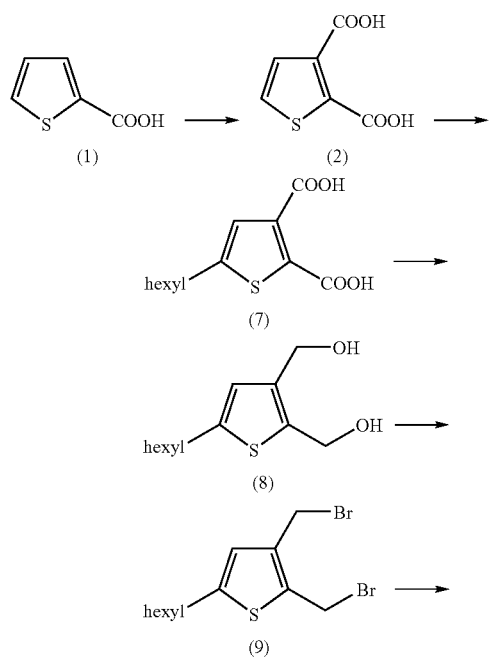

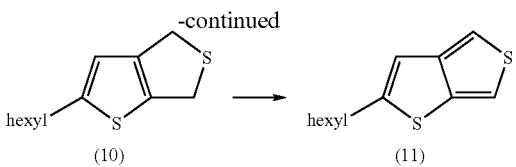

Thiophene-2,3-dicarboxylic acid (2) was prepared according to the procedure outlined in Example 1.

5-Hexyl-Thiophene-2,3-dicarboxylic acid (7). To a solution of thiophene-2,3-dicarboxylic acid (2, 10 g, 58.1 mmol), in anhydrous THF (500 mL), at −78° C. was added a 2.5 M solution of n-BuLi in hexane (77 mL, 192 mmol) over a period of 30 mins. The reaction was allowed to stir at −78° C. for another 90 mins. After 90 mins, hexyl iodide (21.5 mL, 87.15 mmol) was added drop-wise and the reaction continued for another 8 hrs at room temperature. The reaction was quenched by adding 10 mL of water. Approximately 80% THF was removed and made the aqueous layer basic by dilute NaOH solution (color: Orangish). The aqueous layer was extracted twice with diethyl ether to remove excess hexyl iodide which is soluble in ether. The aqueous layer was acidified with dilute HCl (color: Yellowish Cloudy) and extracted with diethyl ether until the aqueous layer became clear. The organic layer was washed with plenty of water to remove excess HCl. The combined organic layers were dried over MgSO$_4$ and concentrated to a crude orange solid 7 (11.9 g, 80% yield). No purification was required in this step.

5-Hexyl-2,3Bis(hydroxymethyl)thiophene (8). To a slurry of LiAlH$_4$ (7.5 g, 195 mmol), in THF (400 mL) at 0° C., under an atmosphere of nitrogen, was added 5-hexyl-thiophene-2-3-dicarboxylic acid (7, 10 g, 39 mmol). The reaction was allowed to warm to 70° C. and was stirred for another 24 hrs. After 24 hrs the reaction flask was kept in ice bath and then 50 mL of diethyl ether was added followed by the addition of 15 mL of water and 15 mL of 10% NaOH solution. Addition of water was drop-wise. The organic layer was dried over MgSO$_4$, filtered and the filtrate concentrated to a crude solid 8 (6.67 g, 75% yield) confirmed by $^1$H-NMR and GC-MS.

5-Hexyl-2,3Bis(bromomethyl)thiophene (9). To a solution of 5-hexyl-2,3 bis(hydroxymethyl) thiophene (8, 10 g, 43 mmol) in anhydrous ether (300 mL) at 0° C., under a nitrogen atmosphere, was added PBr$_3$ (6.15 mL, 65.7 mmol) drop-wise over a period of 15 mins. The reaction was continued for another 6 hrs at room temperature and quenched by adding 50 mL of water. The organic layer was extracted 4-5 times with water until the pH became neutral. The organic layer was dried over MgSO$_4$, filtered and the filtrate concentrated to a crude solid 9 (12.4 g, 80% yield) confirmed by $^1$H-NMR and GC-MS.

2-Hexyl-dihydrothieno[3,4-b]thiophene (10). To a solution of sodium sulfide nonahydrate (6.7 g, 28 mmol) in DMF (300 mL) at 30° C. under a nitrogen atmosphere, was added 5-hexyl-2,3 bis(bromomethyl)thiophene (9, 10 g, 28.2 mmol) solution in DMF (100 mL). 5-Hexyl-2,3 bis(bromomethyl) thiophene addition was very slow and the temperature monitored to gradually increase from 30° C. to 70° C. The reaction was continued for another 12 hrs at 70° C. during which time the contents became dark in color. The product was extracted in diethyl ether (200 mL) and washed with sufficient water to remove DMF. The organic layer was dried over MgSO$_4$, filtered and the filtrate concentrated to a crude dark brown liquid 10 (2.5 g, 40% yield), confirmed by GC-MS.

2-Hexyl-thieno[3,4-b]thiophene (11). 2-Hexyl-dihydrothieno[3,4-b]thiophene (10, 5 g, 22.7 mmol) and anhydrous methylene chloride (100 mL) were taken in a dry 3-neck flask, and cooled the solution to 0° C. before adding DDQ (5.2 g, 22.7 mmol). The reaction mixture was stirred at 0° C. for 30 minutes, and then passed through the silica. After evaporating the solvent, the product was purified by liquid chromatography using petroleum ether as an eluent. The purified product was obtained in 50% yield and confirmed by $^1$H-NMR and GC-MS.

Example 3

Preparation of 2-dodecylthieno[3,4-b]thiophene

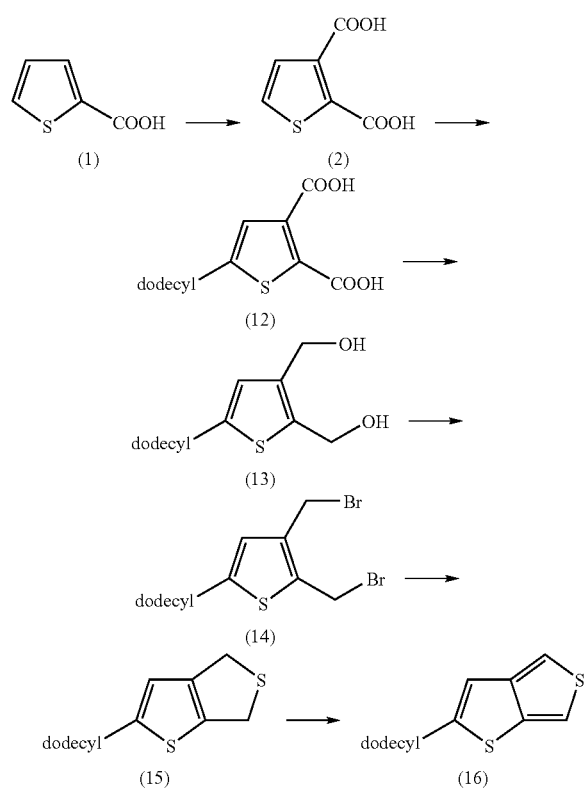

Thiophene-2,3-dicarboxylic acid (2) was prepared according to the procedure outlined in Example 1.

5-Dodecyl-Thiophene-2,3-dicarboxylic acid (12). To a solution of thiophene-2,3-dicarboxylic acid (2, 10 g, 58.1 mmol), in anhydrous THF (500 mL), at −78° C. was added a 2.5 M solution of n-BuLi in hexane (77 mL, 192 mmol) over a period of 30 mins. The reaction was allowed to stir at −78° C. for another 90 mins. After 90 mins, dodecyl iodide (21.5 mL, 87.15 mmol) was added drop-wise and the reaction continued for another 8 hrs at room temperature. The reaction was quenched by adding 10 mL of water. Approx. 80% THF was removed and made the aqueous layer basic by dilute NaOH solution (color: Orangish). The aqueous layer was extracted twice with diethyl ether to remove excess dodecyl iodide, which is soluble in ether. The aqueous layer was acidified with dilute HCl (color: Yellowish Cloudy) and extracted with diethyl ether until the aqueous layer became clear. The organic layer was washed with sufficient water to remove excess HCl. The combined organic layers were dried over MgSO$_4$ and concentrated to a crude orange solid 12 (15.8 g, 80% yield) confirmed by $^1$H-NMR. No purification was required in this step.

5-Dodecyl-2,3Bis(hydroxymethyl)thiophene (13). To a slurry of LiAlH$_4$ (10 g, 263 mmol), in THF (400 mL) at 0° C., under an atmosphere of nitrogen, was added 5-dodecyl-thiophene-2,3-dicarboxylic acid (12, 15 g, 44.1 mmol). The reaction was allowed to warm to 70° C. and was stirred for another 24 hrs. After 24 hrs, the reaction flask was kept in an ice bath and then 50 mL of diethyl ether was added, followed by the addition of 15 mL of water and 15 mL of 10% NaOH solution. Addition of water was drop-wise. The organic layer was dried over MgSO$_4$, filtered and the filtrate concentrated to a crude solid 13 (10.3 g, 75% yield) confirmed by $^1$H-NMR.

5-Dodecyl-2,3 Bis(bromomethyl)thiophene (14). To a solution of 5-dodecyl-2,3bis(hydroxymethyl)thiophene (13, 10 g, 32 mmol) in anhydrous ether (300 mL) at 0° C., under a nitrogen atmosphere, was added PBr$_3$ (4.5 mL, 48 mmol) drop-wise over a period of 15 mins. The reaction was continued for another 6 hrs at room temperature and quenched by adding 50 mL of water. The organic layer was extracted 4-5 times with water until the pH became neutral. The organic layer was dried over MgSO$_4$, filtered and the filtrate concentrated to a crude solid 14 (11.2 g, 80% yield) confirmed by $^1$H-NMR.

2-Dodecyl-dihydrothieno[3,4-b]thiophene (15). To a solution of sodium sulfide nonahydrate (6.5 g, 27 mmol) in DMF (300 mL) at 30° C. under a nitrogen atmosphere, was added 5-dodecyl-2,3 bis(bromomethyl)thiophene (14, 10 g, 22.83 mmol) solution in DMF (100 mL). 2,3 Bis(bromomethyl) thiophene addition was very slow and the temperature monitored to gradually increase from 30° C. to 70° C. The reaction was continued for another 12 hrs at 70° C. during which time the contents became dark in sufficient of water to remove DMF. The organic layer was dried over MgSO$_4$, filtered and the filtrate concentrated to a crude dark brown liquid 15 (3.5 g, 76% yield) confirmed by GC-MS.

2-Dodecyl-thieno[3,4-b]thiophene (16). 2-Dodecyl-dihydrothieno[3,4-b]thiophene (15, 5 g, 16.12 mmol) and anhydrous methylene chloride (100 mL) were taken in a dry 3-neck flask, and cooled the solution to 0° C. before adding DDQ (3.66 g, 16.12 mmol). The reaction mixture was stirred at 0° C. for 30 minutes, and then passed through the silica. After evaporating the solvent, the product was purified by liquid chromatography using petroleum ether as an eluent. The purified product 16 was obtained in 50% yield and confirmed by $^1$H-NMR and GC-MS.

Example 4

Preparation of thieno[3,4-b]tfuran

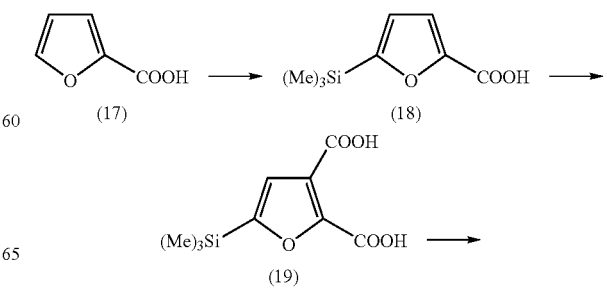

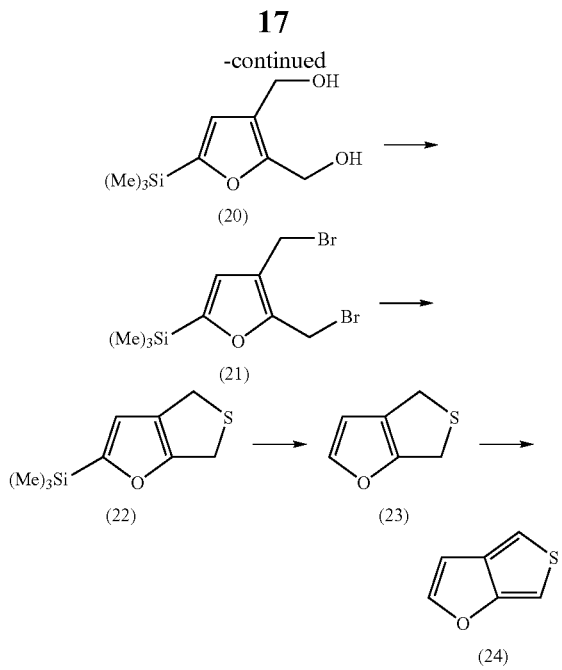

5-TMS-Furan-2-Carboxylic acid (18). To a solution of furan-2-carboxylic acid (17, 20 g, 178 mmol), in anhydrous THF (600 mL), at −78° C. was added a 2.0 M solution of LDA (Lithium Diisopropylamide) in hexane (178 mL, 357 mmol) over a period of 90 mins. The reaction was allowed to stir at −78° C. for another 60 mins. After 60 mins, TMS-Cl (chloro trimethyl silane) (25 mL, 196 mmol) was added to the reaction mixture. The reaction was allowed to warm at room temperature and continued the stirring for another 8 hrs. The reaction was quenched by 200 mL of water and 80% THF was removed by using rotovap. The aqueous layer was acidified with dilute HCl (until cloudy) and extracted with ethyl acetate until the aqueous layer became clear. The organic layer was washed with sufficient water (at least 4-5 times) to remove excess HCl and unreacted starting material. The organic layer was dried over $MgSO_4$ and concentrated to a crude dark brown solid 18 (28 g, 85% yield), confirmed by $^1$H-NMR.

5-TMS-Furan-2-3-dicarboxylic acid (19). To a solution of 5-TMS-furan-2-carboxylic acid (18, 20 g, 108 mmol), in anhydrous THF (600 mL), at −78° C. was added a 2.5 M solution of n-BuLi in hexane (100 mL, 250 mmol) over a period of 30 mins. The reaction was allowed to stir at −78° C. for another 2 hrs at which time it was quenched with $CO_2$. It should be noted that upon addition of $CO_2$, the reaction became very thick and required some shaking for efficient mixing. The reaction was allowed to warm at room temperature and continued the stirring for 8 hrs. The reaction was quenched by 200 mL of water and 80% THF was removed by using rotovap. The aqueous. layer was acidified with dilute HCl (until cloudy) and extracted with ethyl acetate until the aqueous layer became clear. The organic layer was washed with sufficient water (at least 4-5 times) to remove excess HCl. The organic layer was dried over $MgSO_4$ and concentrated to a crude light brown solid 19 (21 g, 85% yield), confirmed by $^1$H-NMR.

5-TMS-2,3Bis(hydroxymethyl)furan (20). To a slurry of $LiAlH_4$ (12.5 g, 329 mmol), in THF (400 mL) at 0° C., under an atmosphere of nitrogen, was added 5-TMS-furan-2-3-dicarboxylic acid (19, 15 g, 65.8 mmol). The reaction was allowed to warm to 70° C. and was stirred for another 24 hrs. After 24 hrs the reaction flask was kept in an ice bath and then 50 mL of diethyl ether was added followed by the addition of 15 mL of water and 15 mL of 10% NaOH solution. Addition of water was drop-wise. The organic layer was dried over $MgSO_4$, filtered and the filtrate concentrated to a crude solid 20 (9.8 g, 75% yield).

5-TMS-2,3Bis(bromomethyl)furan (21). To a solution of 5-TMS-2,3bis(hydroxymethyl)furan (20, 10 g, 32 mmol) in anhydrous ether (300 mL) at 0° C., under a nitrogen atmosphere, was added $PBr_3$ (4.5 mL, 48 mmol) drop-wise over a period of 15 mins. The reaction was continued for another 6 hrs at room temperature and quenched by adding 50 mL of water. The organic layer was extracted 4-5 times with water until the pH became neutral. The organic layer was dried over $MgSO_4$, filtered and the filtrate concentrated to a crude solid 21 (11.2 g, 80% yield), confirmed by GC-MS.

5-TMS-dihydrothieno[3,4-b]furan (22). To a solution of sodium sulfide nonahydrate (7.3 g, 30.4 mmol) in DMF (150 mL) at 30° C. under a nitrogen atmosphere, was added 5-TMS-2,3bis(bromomethyl)thiophene (21, 10 g, 30.67 mmol) solution in DMF (100 mL). 5-TMS-2,3Bis (bromomethyl)furan addition was very slow and the temperature monitored to gradually increase from 30° C. to 50° C. The reaction was continued for another 12 hrs at 50° C. during which time the contents became dark in color. The product was extracted in diethyl ether (200 mL) and washed with sufficient water to remove DMF. The organic layer was dried over $MgSO_4$, filtered and the filtrate concentrated to a crude dark brown liquid 22 (2.4 g, 40% yield). No purification required.

Dihydrothieno[3,4-b]furan (23). 5-TMS-dihydrothieno[3, 4-b]furan (22, 2.4 g, 12.1 mmol) and anhydrous THF (200 mL) were taken in a dry 3-neck flask under nitrogen atmosphere. The solution was stirred for 10 mins and 1.0 M TBAF (5.4 mL, 18.1 mmol) in THF was added drop-wise over a period of 15 mins. The reaction mixture was stirred for another 6 hrs at 70° C. Then 80% THF was removed by rotovap and acidified with dilute HCl (until cloudy). The aqueous layer was extracted with ethyl acetate until the clear aqueous layer is obtained. The organic layer was washed with plenty of water (at least 4-5 times) to remove excess HCl and dried over $MgSO_4$ and concentrated to a crude dark brown liquid 23 (1.3 g, 90% yield), confirmed by GC-MS.

Thieno[3,4-b]furan (24). Dihydrothieno[3,4-b]furan (23, 1.3 g, 10.3 mmol) and anhydrous methylene chloride (100 mL) were taken in a dry 3-neck flask, and cooled the solution to 0° C. before adding DDQ (2.35 g, 10.3 mmol). The reaction mixture was stirred at 0° C. for 30 minutes, and then passed through the silica. After evaporating the solvent, the product was purified by liquid chromatography using petroleum ether as an eluent. The purified thieno[3,4-b]furan 24 was obtained (0.6 gm, 50% yield) confirmed by $^1$H-NMR and GC-MS.

Example 5

Preparation of regioregular poly(2-dodecylthieno[3,4-b]thiophene)

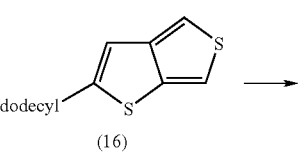

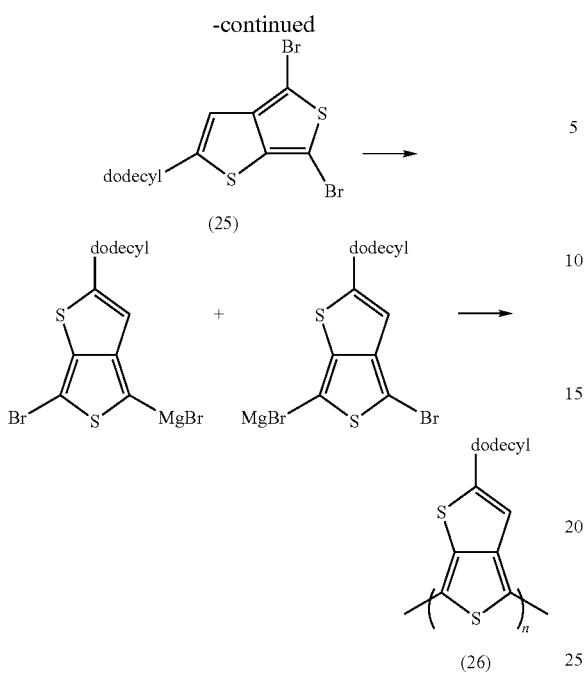

4,6-Dibromo-2-dodecylthieno[3,4-b]thiophene (25). Dodecyl thienothiophene (0.50 g, 1.62 mmol) was dissolved in 50 mL of anhydrous DMF. N-Bromosuccinimide (0.58 g, 3.24 mmol) was added to the solution over a period of 5 minutes. The solution was stirred at 0° C. for 4 hours then 100 ml of water was added and product was extracted into diethyl ether. The diethyl ether layer was washed with 100 mL portions of water for 5 times to remove DMF. The diethyl ether layer was dried over $MgSO_4$ and the solvent was removed in vacuo. The product (0.60 g, 80%) was obtained as a white solid and confirmed by $^1$H-NMR.

Regioregular poly(2-dodecylthieno[3,4-b]thiophene) (26). 4,6-Dibromo-2-dodecylthieno[3,4-b]thiophene (0.1 gm, 0.214 mmole) was dissolved in 10 mL of dry THF. Hexylmagnesium bromide (0.21 mL, 1.0 M solution in diethyl ether) was added and the mixture was kept at 10° C. for 1 h. (To confirm the formation of Grignard product an aliquot was taken out from the reaction mixture, quenched with water and analyzed by GC/MS and $^1$H-NMR.). Ni(dppp)$Cl_2$ (0.5-1 mole %, 0.58-1.16 mg) was added and the solution was stirred for 2 h at different conditions (0.5 mole % catalyst at 10° C.; 1 mole % at 10° C.; and 1 mole % at reflux). The mixture was poured into 100 mL of methanol and filtered into a Soxhlet thimble. Soxhlet extractions were performed with methanol (to remove monomer and salts), hexanes (to remove catalyst and oligomers), and chloroform. The chloroform fraction was reduced and dried in vacuum to obtain the polymer (1 mole % catalyst at reflux) as a dark brown film or an oligomer (0.5-1 mole % catalyst at 10° C.). The product was confirmed by $^1$H-NMR and GC-MS.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. "Or" means and/or. Recitation of ranges of values herein are merely intended to serve as a shorthand method of referring individually to each separate value falling within the range, unless otherwise indicated herein, and each separate value is incorporated into the specification as if it were individually recited herein. All ranges disclosed herein are inclusive and combinable.

The essential characteristics of the present invention are described completely in the foregoing disclosure. One skilled in the art can understand the invention and make various modifications without departing from the basic spirit of the invention, and without deviating from the scope and equivalents of the claims, which follow. Moreover, any combination of the above-described elements in all possible variations thereof is encompassed by the invention unless otherwise indicated herein or otherwise clearly contradicted by context.

What is claimed is:

1. A method of making a fused heterocycle, comprising:
carboxylating the 3 position of a compound of formula I or a suitably protected derivative thereof

to form a dicarboxylic acid compound; and
converting the dicarbocylic acid compound to a fused heterocycle of formula (II)

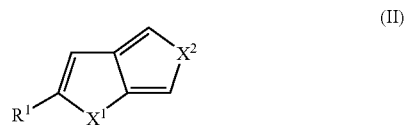

wherein $X^1$ is S, O, N—$R^1$, or P—$R^2$, wherein $R^1$ is hydrogen or a nitrogen protecting group, and $R^2$ is hydrogen or a phosphorus protecting group;

$X^2$ is S, O, N—$R^1$, or P—$R^2$ where $R^1$ and $R^2$ are as previously defined; and R is hydrogen, $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, nitro, halo, amino, or mono- or di alkyl amino.

2. The method of claim 1, wherein $X^1$ is S or O and $X^2$ is S or O such that compounds according to formula II are

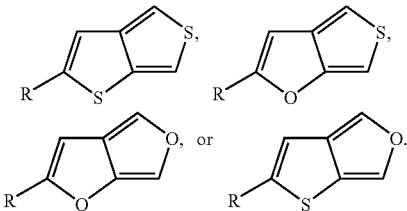

3. The method of claim 1, wherein R is hydrogen or $C_1$-$C_{20}$ alkyl.

4. The method of claim 1, wherein R is $C_6$-$C_{12}$ alkyl.

5. The method of claim 1, further comprising:
reducing the carboxylic acid groups of the dicarboxylic acid compound to form a compound comprising hydroxyl groups;
converting the hydroxyl groups into leaving groups to form an intermediate compound;

cyclizing the intermediate compound to form a dihydro derivative of formula II; and
aromatizing the dihydro derivative of formula II to form a fused heterocycle of formula II.

6. The method of claim 1, wherein the carboxylating is carried out with carbon dioxide, formic acid, or a chloroester-formate.

7. The method of claim 5, wherein the reducing is carried out using lithium aluminum hydride (LiAlH$_4$), borane, aluminum hydride, or samarium (II) iodide (SmI$_2$) in basic media.

8. The method of claim 5, wherein the converting the hydroxyl groups to leaving groups involves
halogenation using thionyl chloride, PCl$_3$, PCl$_5$, POCl$_3$, PBr$_3$, PBr$_5$, the combination of PPh$_3$ and CCl$_4$ or the combination of PPh$_3$ and CBr$_4$; or
the preparation of alkyl or aryl sulfonates.

9. The method of claim 5, wherein the cyclizing to form
a dihydrothienyl moiety involves treatment of the intermediate compound with sodium sulfide or a hydrate thereof, or hydrogen sulfide;
a dihydrofuranyl moiety involves treatment of the intermediate compound with hydroxide or an oxide ion;
a dihydropyrrolyl moiety involves treatment of the intermediate compound with a sodium or calcium salt of cyanamide NH$_2$—CN; or
a dihydrophospholyl moiety involves treatment of the intermediate compound with a phosphine or a monoalkylsubstituted phosphine.

10. The method of claim 5, wherein the aromatizing of the dihydro derivative of formula II involves use of 2,3-dichloro5,6-dicyano-1,4-benzoquinone (DDQ), 2,3,5,6-tetrachloro-1,4-benzoquinone (chloranil), oxygen, MnO$_2$, SeO$_2$, or chromic acid.

11. The method of claim 5, further comprising derivatizing the dicarboxylic acid compound at the 5 position.

12. The method of claim 11, wherein the derivatizing is carried out using electrophilic or nucleophilic chemistries.

13. The method of claim 11, wherein the derivatizing is carried out by a metallation reaction followed by an alkylation using a haloalkyl having 1-20 carbon atoms.

14. The method of claim 5, further comprising protecting the 5 position of the compound of formula I prior to carboxylating; and deprotecting the 5 position prior to aromatizing or prior to reducing the carboxylic acid groups.

15. The method of claim 5, wherein the 5 position is protected with a silyl protecting group.

16. The method of claim 14, further comprising derivatizing the dicarboxylic acid compound at the 5 position after deprotecting.

17. The method of claim 16, wherein the derivatizing is carried out using electrophilic or nucleophilic chemistries.

18. The method of claim 16, wherein the derivatizing is carried out by a metallation reaction followed by an alkylation using a haloalkyl having 1-20 carbon atoms.

19. A regioregular polymer, comprising:
a regioregular fused heterocycle polymer of formula (III)

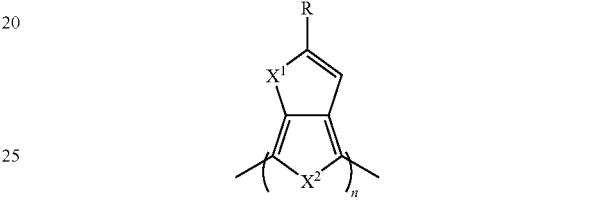

(III)

wherein X$^1$ is S, O, N—R$^1$ or P—R$^2$, wherein R$^1$ is hydrogen or a nitrogen protecting group, and R$^2$ is hydrogen or a phosphorus protecting group;
X$^2$ is S, O, N—R$^1$, or P—R$^2$ where R$^1$ and R$^2$ are as previously defined; and
R is C$_1$-C$_{20}$ alkyl, C$_1$-C$_{20}$ haloalkyl, aryl, heteroaryl, C$_1$-C$_{20}$ alkoxy, C$_1$-C$_{20}$ haloalkoxy, aryloxy, —C$_1$-C$_{10}$ alkyl-O—C$_1$-C$_{10}$ alkyl, —C$_1$-C$_{10}$ alkyl-O-aryl, nitro, halo, amino, or mono- or di alkyl amino.

20. An article comprising the polymer of claim 19.

* * * * *